United States Patent [19]

Fleck

[11] Patent Number: 5,699,794
[45] Date of Patent: Dec. 23, 1997

[54] APPARATUS FOR AUTOMATED URINE SEDIMENT SAMPLE HANDLING

[75] Inventor: Thomas M. Fleck, Woodinville, Wash.

[73] Assignee: NeoPath, Inc., Redmond, Wash.

[21] Appl. No.: 574,661

[22] Filed: Dec. 19, 1995

[51] Int. Cl.$^6$ ............................................. A61B 5/00
[52] U.S. Cl. ........................................ 128/633; 128/920
[58] Field of Search ......................... 364/413.02, 413.11

[56] References Cited

U.S. PATENT DOCUMENTS

| | | |
|---|---|---|
| 3,731,806 | 5/1973 | McCormick . |
| 3,775,595 | 11/1973 | Resse et al. ............... 364/413.11 |
| 3,894,845 | 7/1975 | McDonald . |
| 3,988,209 | 10/1976 | McDonald . |
| 4,058,367 | 11/1977 | Gilford ...................... 364/413.11 |
| 4,133,642 | 1/1979 | Nosaka et al. ............. 364/413.11 |
| 4,393,466 | 7/1983 | Deindoerfer et al. . |
| 4,473,530 | 9/1984 | Villa-Real . |
| 4,612,614 | 9/1986 | Deindoerfer et al. . |
| 4,622,298 | 11/1986 | Mansour et al. . |
| 4,804,267 | 2/1989 | Greenfield . |
| 4,852,025 | 7/1989 | Herpichbohm . |
| 4,853,551 | 8/1989 | Wagner et al. . |
| 4,973,450 | 11/1990 | Schluter . |
| 5,121,436 | 6/1992 | Kasdan et al. . |
| 5,132,232 | 7/1992 | Parker . |
| 5,137,031 | 8/1992 | Guirguis . |
| 5,192,553 | 3/1993 | Boyse et al. . |
| 5,218,645 | 6/1993 | Bacus . |
| 5,287,272 | 2/1994 | Rutenberg et al. . |
| 5,361,140 | 11/1994 | Hayenga et al. . |

OTHER PUBLICATIONS

Deindoerfer, F.H. et al., "The Yellow IRIS™" Urinalysis Workstation—The First Commercial Application of Automated Intelligent Microscopy, *Clinical Chemistry*, vol. 31, No. 9, 1985, pp. 1491–1499.

Haber, Meryl H., "A Primer of Microscopic Urinalysis", Published by ICL Scientific, Fountain Valley, California. ©1978, pp. 1–49.

Ferris, Judith A., "Comparison and Standardization of the Urine Microscopic Examination", *Laboratory Medicine*, 14:10, Oct. 1983, pp. 659–662.

Free, Helen M. et al., "Routine Urinalysis", Proposed Guideline of Jul. 1991, National Committee For Clinical Laboratory Standards, NCCLS No. GP16, vol. 11, No. 12.

Elin, Ronald J., "Comparison of Automated and Manual Methods for Urinalysis", AJCP, Dec. 1986, pp. 731–737.

*Primary Examiner*—William E. Kamm
*Attorney, Agent, or Firm*—Hans I. Sun; Emil Moffa

[57] ABSTRACT

An automated apparatus for urine sediment sample handling includes settling cells for carrying patient samples transported on a sample and cell transport assembly. An illumination and camera assembly is positioned in an examination area to view one of the settling cells when it moves to the examination area. The illumination and camera assembly have a first data output. An image processing assembly is coupled to receive data from the first data output. The image processing assembly have a second data output for carrying processed digital data. A processor having control lines is coupled to the sample and cell transport assembly, illumination and camera assembly, and image processing assembly where the sample and cell transport assembly, illumination and camera assembly, and image processing assembly operate responsively to commands from the processor to handle the urine sediment samples.

9 Claims, 15 Drawing Sheets

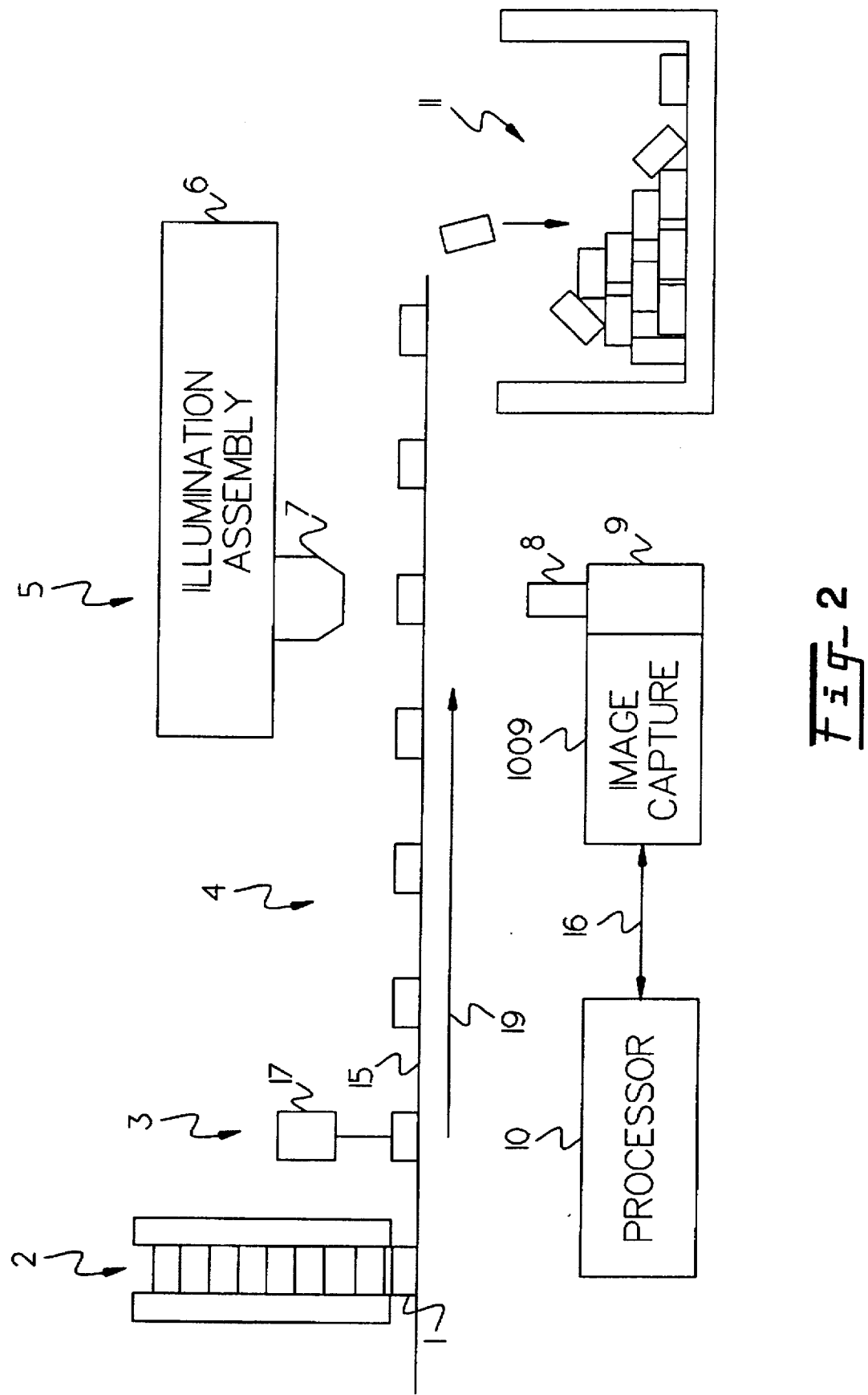

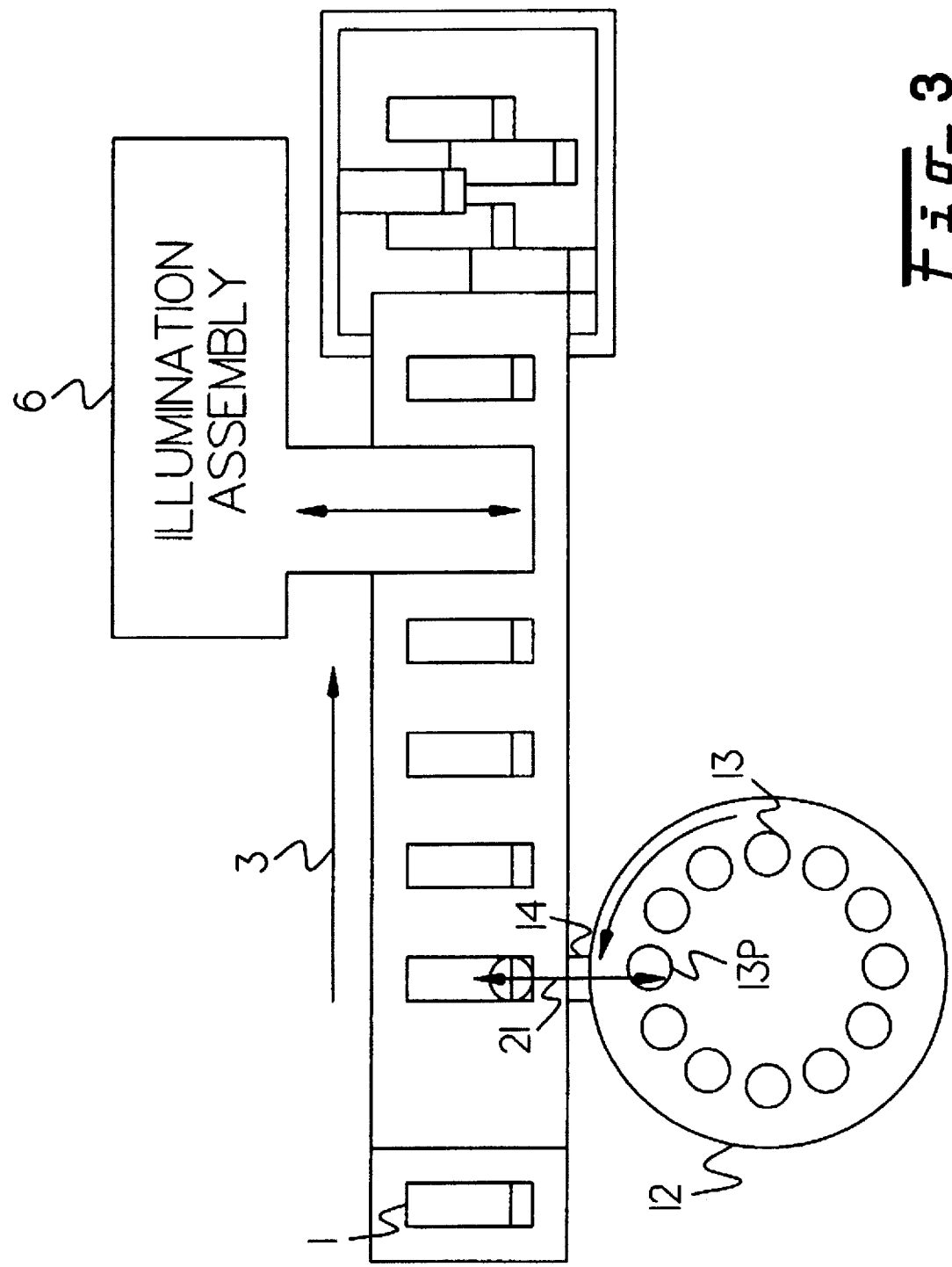

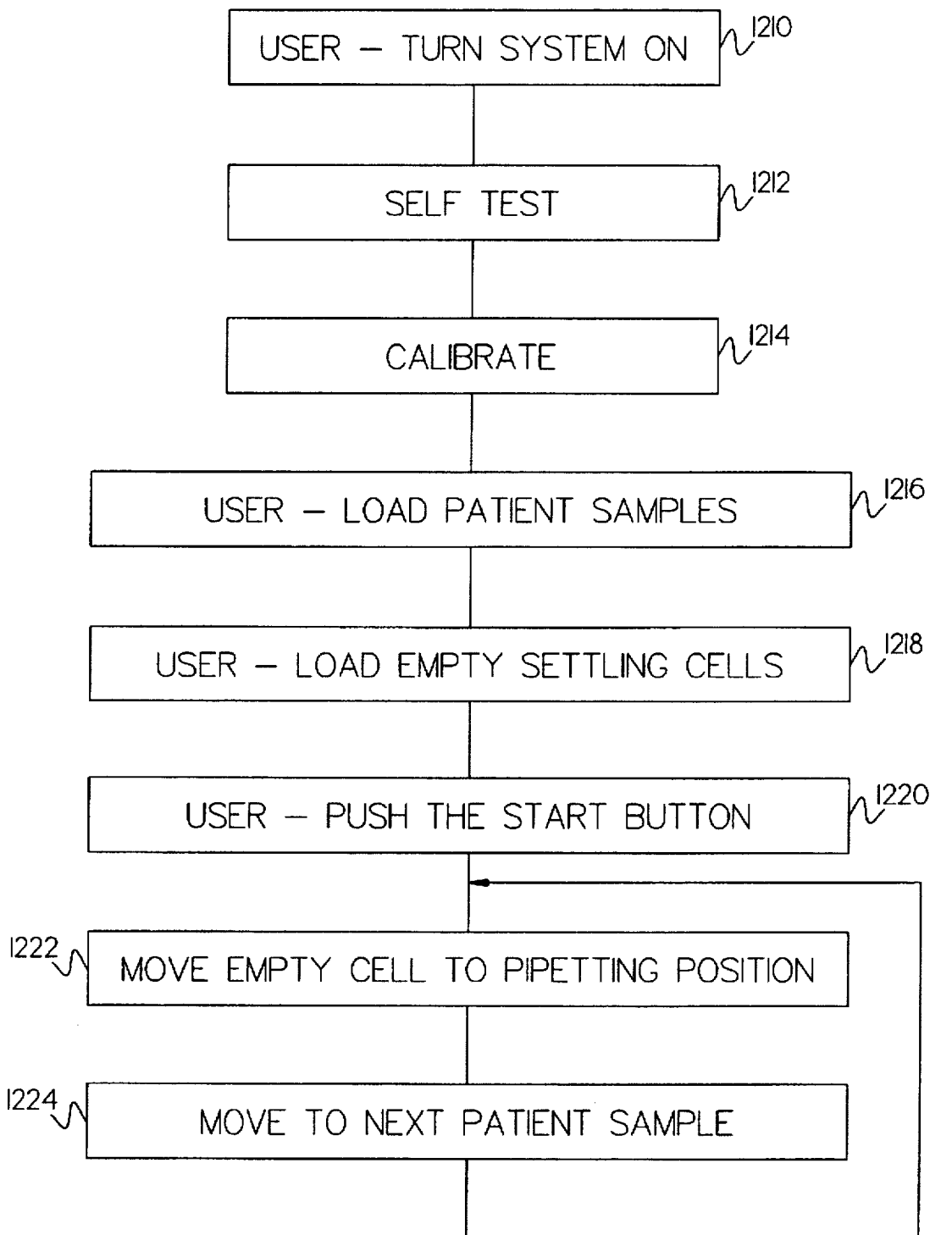

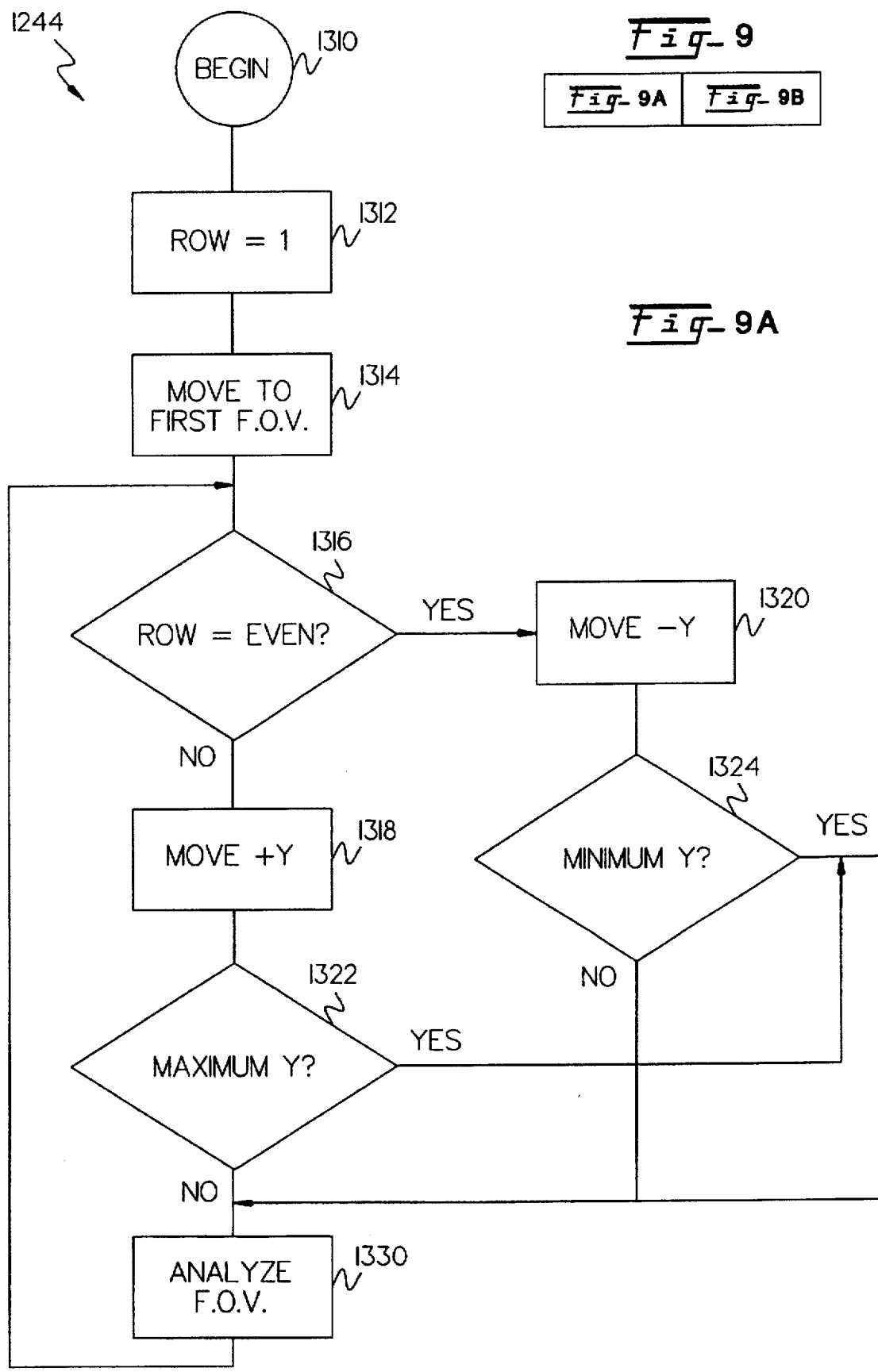

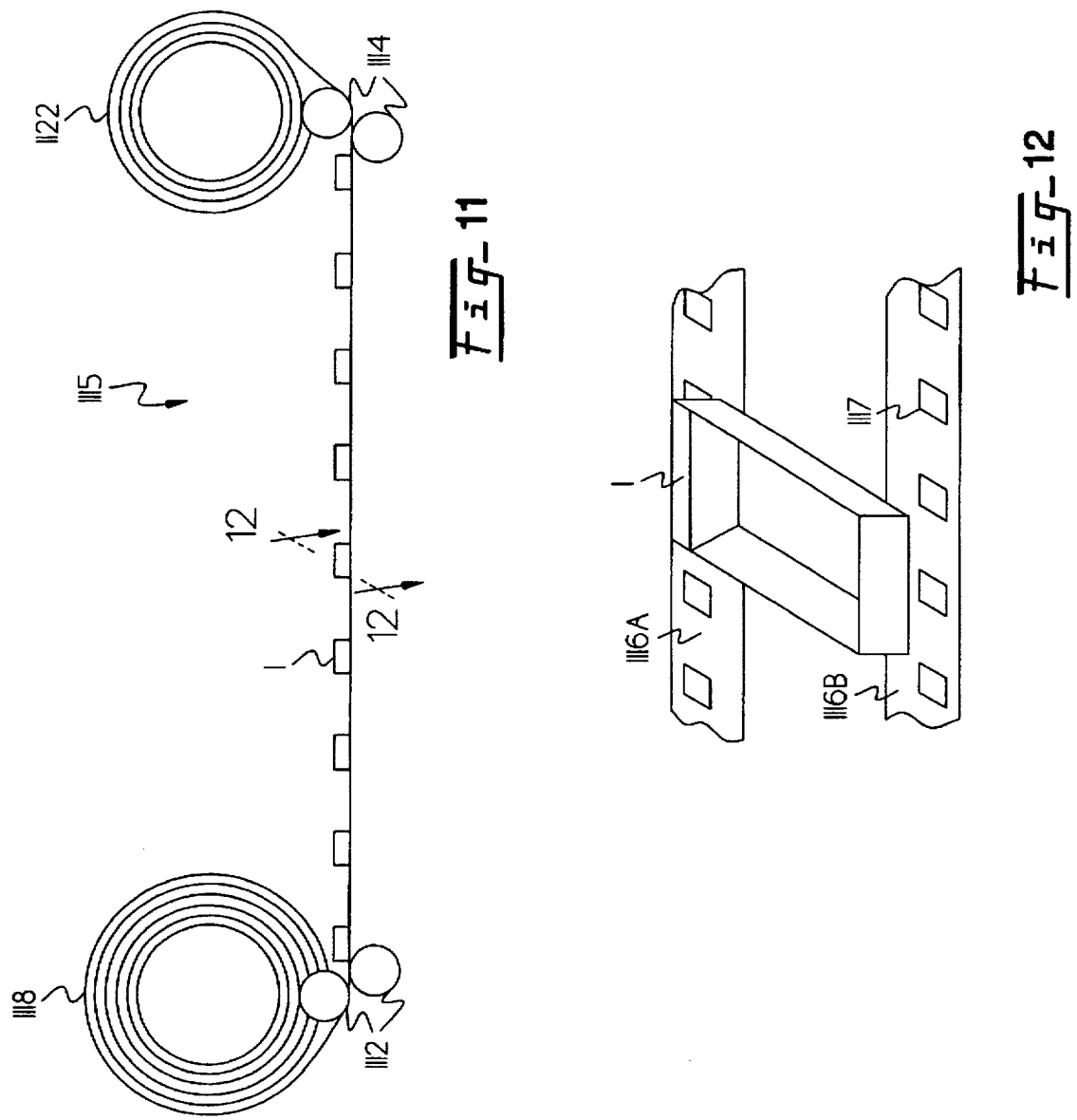

APPARATUS FOR AUTOMATED URINE SEDIMENT SAMPLE HANDLING

FIELD OF THE INVENTION

This invention relates to an automated apparatus for analyzing biological fluids, and more particularly to an automated apparatus for handling urine sediment samples.

BACKGROUND OF THE INVENTION

Examination of urine sediment is predominantly done manually by the use of an optical microscope. Some types of semi-automated systems have been developed, but these still require visual analysis by a highly trained technician. The current state of the art in the field of analysis of urine sediments includes several methods as implemented by various laboratories.

The three methods that generally represent the state of the art include a microscope slide method using a standard microscope slide and cover slip viewed through a microscope, a KOVA® chamber method using specialized, gridded holding chambers, and a partially automated flow cell method. Such prior art methods are labor intensive and prone to error.

For example, an article entitled "MHS: Comparison and Standardization of the Urine Microscopic Examination," by Judith A. Ferris, in "Laboratory Medicine" October 1983, Vol. 14, No. 10, 659–662, describes a false-negative rate for three manual methods of urine examination that was shown to be as high as 57%. In this article, a false negative condition was defined as a failure to detect components such as casts, neoplastic cells, and fat bodies, that were actually present in a specimen. Such inaccurate results were obtained by highly trained technologists working in a laboratory environment.

It has been determined by the College of American Pathologists that the mean time to perform a manual urinalysis is 6 minutes per sample. Such a manual urinalysis exam includes up to seven steps. In four of the seven steps the patient sample is handled directly. During each of the handling steps, precautions must be taken to avoid contamination. An automated urine analysis system incorporating the automated handling apparatus of the invention will eliminate most of the specimen handling now required and will perform examinations in less time than currently employed methods.

The microscope slide method of the prior art generally involves following procedures such as may be found in a paper entitled "Routine Urinalysis," Proposed Guideline of July 1991, National Committee for Clinical Laboratory Standards Document No. GP16-P Vol. 11 No. 12., Haber, Meryl H. In following such procedures, a sample is centrifuged for 5 minutes. A portion of supernatant is then removed from the sample. Stain may be added to improve the sample contrast. The sample is re-suspended. A portion of the sample is removed and placed on a glass microscope slide covered by a glass cover slip. The prepared slide is examined under an optical microscope. The examination may be done at low power (usually 100X) first in order to direct a high power (usually 400X) examination. Objects are classified into various types and the number of objects of each type is reported in terms of the number of objects per high power field. At least 10 high power fields are examined.

The KOVA® slide method involves the use of a commercially available kit including a consumable sample holder which is apparently made from pieces of molded plastic. The sample is placed in a cavity in the consumable sample holder. The sediment is examined in this cavity. The geometry of the sample cavity may be controlled. A sample is prepared and placed in a centrifuge at Relative Centrifuge Force (RCF) of 400 for 5 minutes. Supernatant is decanted using a pipetter device that is supplied in the manufacturer's kit. The sample is resuspended and stain is added, if desired. A portion of the sample is transferred to the sample chamber of the consumable sample holder. The prepared sample is examined under an optical microscope. An initial examination may be done at low power, usually 100X, in order to direct a high power examination. Objects may be classified into various types and the number of objects of each type may be reported in terms of the number of objects per a predetermined volume. The number of objects per the predetermined volume may be determined by counting the number of objects within each grid and applying a known conversion factor supplied by the manufacturer.

U.S. Pat. No. 4,612,614 to Deindoerfer, et al., entitled "Method of Analyzing Particles in a Fluid Sample", discloses a method for analyzing urinary sediments by distributing a sample over an extended area, such as a microscope slide or a flow cell. Deindoerfer, et al. discloses the use of a plurality of optical still images of the sample that are converted into electronic images which are displayed in an array ordered by classes of visually discernable characteristics.

The flow cell method generally follows the following procedure, as described by Deindoerfer et al. In the Deindoerfer et al. method, a portion of the sample is transferred to a container. The sample is forced through a glass aperture which is designed to orient the sediment in a plane for viewing. The sediment is examined by using a CCD video camera as the sediment flows by. The sediment is illuminated by a strobe light. After the sample has passed under the video camera a video image is created. The sample is disposed of through a normal sewer drain. The video image is converted to digital information and stored. The digital information is evaluated via image processing which classifies each object according to size and shape. The images of the objects are presented on a video display to a technologist to be classified and counted. The flow cell is flushed out before the next sample is processed.

The related art methods described as the microscope slide method and the KOVA® slide method include a centrifugation step in order to concentrate the sediment in the sample. The centrifugation process requires several steps which may cause inconsistency. For example, fluid volume in a sample is generally not very well controlled and any variation in fluid volume may cause a variation in the final concentration. The amount of supernatant extracted is also not well controlled. See, for example, Ferris, J., "Comparison and Standardization of the Urine Microscopic Examination", *Laboratory Medicine*, 14:10, pp. 659–662, October 1983. The volume of supernatant removed is critical since it determines the amount of fluid that remains and therefore the concentration. Finally the resuspension process is not well controlled even though it has a large effect on the final concentration.

Currently available methods do not adequately address a tendency for sediments to concentrate towards the periphery of a sample. Due to capillary forces, most of the sediment tends to collect in the periphery of the drop of sample when it is placed on the slide. This effect is well known. Common practice in the related art involved examination of the periphery of the sample while ignoring the center. This related art practice rendered determination of concentration of objects per volume of fluid virtually impossible. This is also discussed by Ferris, ibid. Further, the area of the field of view may not be consistent for all microscopes even at the same magnification, therefore the relationship between the number of objects within a field and the concentration may be unknown. The compressed height of the fluid under the coverslip on the slide is not controlled. As a result, any measurement of concentration is unreliable.

The three methods specifically described above further include a step in which objects are counted in a small portion of the original sample. Uncertainty introduced due to such a sampling process may be determined by using a Poison statistical model. For an example of such a model see Gadeholt, H., "Counting of Cells in Urine: The Variability of Hemocytometer Counts", ACTA Med. Sc. 183, 9–16, 1968. For a Poison process, the standard deviation of the number of objects counted is equal to the square root of the mean. The number of white blood cells typically present in normal urine is 5 cells per field. In both of the manual microscopy methods, 10 fields are examined. Therefore, for an abnormal patient there should be more than 50 white cells counted during the examination. The resulting coefficient of variation (CV) is about Since the Deindoerfer et al. method, for example, does not concentrate the objects, the number of objects counted is even less. The CV for the Deindoerfer method et al. method at a concentration of 5 cells per field is about 30%. Each of the above-described known methods includes a step in which a technologist must examine a sample to classify and count the objects. As a result, such an analysis is subject to human errors, fatigue, and human bias. In contrast, the present invention employs a method that counts 100 cells when there are 5 cells per field. Therefore, the CV is about 10%.

Several other techniques for examining urine sediment have also been developed. For example, U.S. Pat. No. 5,137,031 to Guirguis, entitled "Urine Testing Apparatus With Urinary Sediment Device", discloses an apparatus for collecting urinary sediments from urine and for concentration and detection of specific antigens in a biological fluid such as urine. Guirguis discloses a device having two removable sealable units. The first unit is a urinary sediment/ antigen container having two chambers separated by a perforated support system that sandwiches a filtration membrane allowing for bi-directional flow of fluid through the filtration membrane. The top chamber contains gel chromatography beads while a lower chamber is designed to retain the urinary sediments. A second unit is a cytology sedimentation cup that attaches to the bottom of the first unit. However, Guirguis does not provide for detection of the concentration of sediments within a given volume of urine. Guirguis also does not disclose an apparatus for automatically analyzing urine sediment.

U.S. Pat. No. 5,121,436 to Kasdan, et al., entitled "Method and Apparatus for Generating a Plurality of Parameters of an Object in a Field of View", discloses an apparatus that generates a plurality of parameters for an object within a field of view. Kasdan forms an electrical image of the field of view and processes the electrical image to form a plurality of different representations. The parameters that Kasdan, et al. determines include the area, mass density and shape.

U.S. Pat. No. 4,853,551 to Wagner, et al., entitled "Safety Interlock For X-Ray Particle Size Analyzer", discloses an x-ray sedimentation particle size analyzer where data is taken at particular positions along the sedimentation cell. Wagner, et al. provides for presentation of data in the form of a particle size distribution by using an interpolation technique. Determination of particle size is accomplished by passing a radiation source, preferably x-rays, through a suspension of the sample. The transmittance of x-rays is recorded and the source is moved along predetermined locations of the cell. The process is repeated until information has been obtained for a desired range of particle sizes.

U.S. Pat. No. 4,804,267 to Greenfield, entitled "System for Microscopically Analyzing Fluids", discloses an apparatus for microscopically analyzing fluids employing fluid flow for acquiring and displaying an image. Greenfield uses a flow cell, where a thin planar portion of the sample is presented for viewing. Greenfield passes a light beam through the flow cell enabling a video camera to acquire a magnified image of a portion of the sample. The image may be displayed on a monitor.

U.S. Pat. No. 4,473,530 to Villa-Real, entitled "Compact Sanitary Urinalysis Unit", discloses a closed integrated system having a number of separated chambers for allowing the testing and analysis of a urine specimen. The compact sanitary urinalysis unit has a lower chamber to accumulate urine sediments after centrifugation. The sediments may then be microscopically examined.

U.S. Pat. No. 3,894,845, entitled "Urine Collection and Analysis Device", and U.S. Pat. No. 3,988,209, entitled "Microorganism Analysis Device", both to McDonald, disclose an apparatus useful for collecting urine and performing analysis on collected specimens. McDonald also discloses a sedimentation tube. The sedimentation tube is designed to be of a conventional size and external shape for fitting in a conventional centrifuge. McDonald discloses a flexible tube attached to the sedimentation tube for syphoning out the sediment to be examined microscopically. McDonald does not disclose an automated apparatus for urine sediment analysis.

U.S. Pat. No. 4,973,450 to Schluter, entitled "Device for Urinalysis", discloses a device for microscopic analysis of urinary sediment. Schluter teaches the concentration of sediment particles in a smaller liquid volume while avoiding centrifugation. Schluter makes use of a cylindrical container having a three filter system.

U.S. Pat. No. 4,852,025 to Herpichbohm, entitled "System for Determining the Concentration of Components of Body Fluids", discloses a system of determining concentration of components of body fluids. The system computes a concentration from information contained on a test carrier along with information on an evaluation curve.

U.S. Pat. No. 3,731,806 to McCormick, entitled "Specimen Analysis Device", discloses a device for separating the biological fluid specimen into liquid and solid constituents. McCormick uses a filter sheet in combination with a vacuum source to draw off a liquid portion of a specimen and leaving the solid constituents on the upper surface of the filter sheet.

U.S. Pat. No. 4,622,298 to Mansour, et al., entitled "Detection and Quantitation of Microorganisms, Leukocytes and Squamous Epithelial Cells in Urine", teaches a method for assessing the three cell types within a sample by staining with a fluorescent dye. Mansour, et al. teaches analyzing the urine specimen directly, preferably by a single flow microfluorometry protocol.

U.S. Pat. No. 5,132,232 to Parker, entitled "Method and Apparatus for Preparation of Liquids for Examination", discloses an apparatus that may collect a urine sediment and stain a sample with dye or react with an agent as necessary without disturbing the sample within the apparatus. Parker is designed to be used in combination with centrifugation.

SUMMARY OF THE INVENTION

The invention provides an automated apparatus for urine sediment sample handling. A transport assembly moves a plurality of settling cells containing patient samples in one direction. An illumination and camera assembly is positioned in an examination area to view one of the plurality of settling cells when a settling cell moves under the examination area. The illumination and camera assembly has a first data output. An image processing assembly is coupled to receive data from said data output, the image processing assembly having a second data output for carrying processed digital data. A processor having a plurality of control lines is coupled to said sample and cell transport assembly, illumination and camera assembly, and image processing assembly wherein said sample and cell transport assembly, illumination and camera assembly, and image processing assembly operate responsively to commands from said processor to handle the urine sediment samples.

The invention provides for an automated apparatus for handling urine sediments including those that have not been subject to centrifugation.

In contrast to the prior art, the instant invention does not require human examination of urine sediment. Since the present invention provides automated handling apparatus for urine sediment examinations, the time to do the analysis may be reduced. The only human activity is to transfer a portion of the patient sample to a container which is inserted into a sample container. The transfer into the sample container does not have to be accurate and may be done by a laboratory assistant instead of a highly trained technician.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

FIG. 2 shows a side view of the inventive apparatus for automated urine sediment sample handling of the invention.

FIG. 3 shows a top view of the apparatus for automated urine sediment sample handling of the invention.

FIGS. 11 and 12 show a schematic diagram with an enlarged view of one embodiment of a transport mechanism employing a tape and reel as may be employed in one embodiment of the inventive apparatus for automated urine sediment sample handling of the invention.

DETAILED DESCRIPTION OF THE PREFERRED EMBODIMENT

Figure 1:
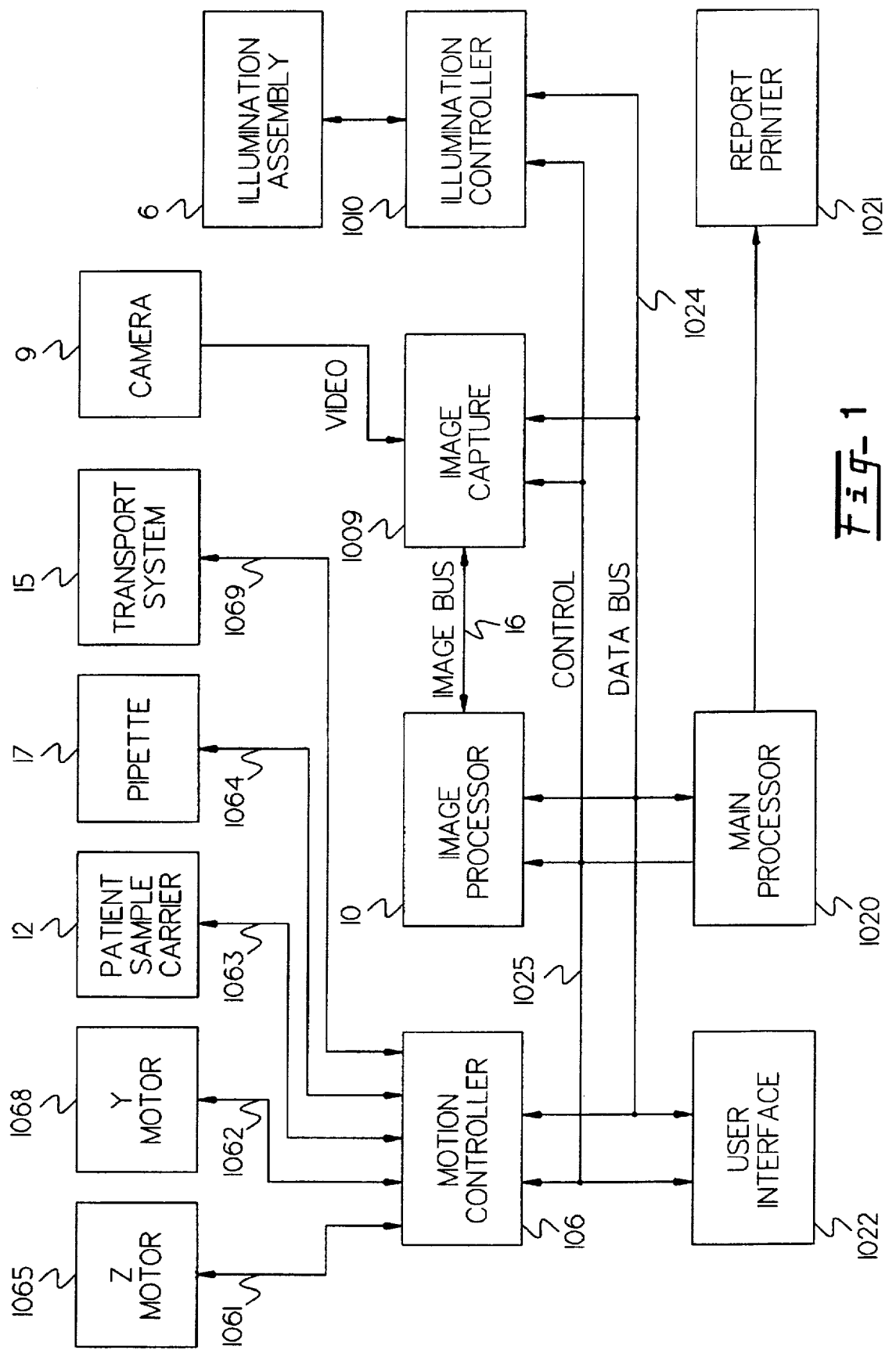
FIG. 1 is a schematic system block diagram of the inventive apparatus for automated urine sediment sample handling of the invention.

Referring now to FIG. 1, a schematic system block diagram of the inventive apparatus for automated urine sediment sample handling of the invention is shown. The apparatus for urine sediment sample handling comprises a motion controller 106, main processor 1020, a user interface 1022, image processor 10, camera 9, illumination controller 1010 and an illumination assembly 6. The motion controller 106 has control lines 1061, 1062, 1063, 1064 and 1069 coupled to a Z motor 1065, a Y motor 1068, a patient sample carrier 12, an automatic pipette 17, and a transport system 15 respectively. The motion controller 106 coordinates timing and movement for the Z motor 1065, Y motor 1068, patient sample carrier 12 and automatic pipette 17 so that samples are handled and analyzed at a desirable rate. The Z motor 1065 and Y motor 1068 may advantageously comprise stepper motors similar to motors employed in computer disc drive assemblies, or other motors or gear arrangements capable of providing movement in a precisely controlled manner.

A data bus 1024 connects the main processor 1020, the motion controller 106, a user interface 1022, image capture apparatus 1009 and the illumination controller 1010. The main processor 1020 further includes control lines 1025. The image processor 10 may advantageously comprise a dedicated high speed processor for executing the process steps discussed hereinbelow. The user interface 1022 may be any well known user interface as, for example, a display and a keyboard having a mouse or equivalent device. The main processor may comprise a conventional computer, personal computer or equivalent computer processor unit such as a microprocessor. The main processor 1020 advantageously contains a software program implementing a process for automated urine sediment sample handling as detailed hereinbelow. The main processor 1020 controls all of the functions of the system, calculates the final results, controls the circuitry which controls all of the various motors, the user interface 1022, and a report printer 1021.

The illumination controller 1010 may be any conventionally designed illumination controller 1010 which serves to automatically adjust the illumination assembly 6 for intensity, uniformity and frequency. The illumination controller 1010 may advantageously be controlled from the main processor 1020.

The camera 9 may advantageously comprise a CCD video camera coupled to the image capture apparatus 1009. The image capture apparatus 1009 may be any well known apparatus for storing a digitized data representation of a video image. The image capture apparatus 1009 may advantageously be coupled to the image processor 10 by an image bus 16. It will be understood that the term "image" as used herein usually refers to digital data derived from a scan of a field of view of the camera 9. Once the scanned image is captured, it is converted into a binary code which may be further processed.

Referring now to FIG. 2, a side view of one example embodiment of apparatus for automated urine sediment sample handling is shown. The apparatus for urine sediment sample handling comprises a settling cell storage area 2, a transport system 15, an automatic pipetting region 3, a settling area 4, a data acquisition area 5, and a disposal area 11. In one example, the transport system 15 may comprise one or more conveyer belts or equivalent means for transporting settling cells 1 in the direction indicated by arrow 19. The settling cell storage area 2 may comprise any dispenser suitable for holding the settling cells 1 and dispensing one unit at a time as needed either on a regular cycle or in response to a control signal. In one embodiment of the invention, the automatic pipetting region 3 comprises the location for the automatic pipette 17 which may be of the type commonly used in medical laboratories. A conventional bar code reader 14 may also be placed adjacent the automatic pipette 17, as best shown in FIG. 3.

In one embodiment of the invention, the data acquisition area 5 may advantageously include the illumination assembly 6, an automatic microscope having a condenser lens 7 and an objective lens 8, and the video camera 9. The video camera 9 may advantageously comprise a CCD video camera or equivalent data acquisition device. The illumination assembly 6 may advantageously comprise a strobe light or equivalent illumination device.

The illumination assembly 6, condenser lens 7, objective lens 8, and video camera 9 may advantageously be optically arranged so that the illumination assembly 6 illuminates the settling cells 1 through the condenser lens 7 and the image of any sediment within the cell is captured through the objective lens 8 by the video camera 9. An image processor 10 is coupled to receive data from the video camera 9 and image capture apparatus 1009 by image bus 16.

Now referring to FIG. 3, patient sample containers 13 are stored in a sample carrier 12. The patient sample containers 13 are stored with open tops so as to allow access for the automatic pipette 17. The sample carrier may advantageously be a revolving carousel or other equivalent arrangement capable of holding patient samples 13 and moving a series of samples into place for pipetting as each new settling cell is positioned in the automatic pipetting region 3. The automatic pipette 17 may advantageously be constructed so as to move in an oscillating manner as indicated by double arrow 21. In this way, the automatic pipette 17 may be positioned over a sample in the sampling position 13P for obtaining a fluid sample and then returning to dispense the obtained sample into a settling cell filling hole 32 shown in FIG. 4A.

In operation, when a barcode is detected by the barcode reader 14, the automatic pipette 17 removes a portion of the sample and dispenses it into the settling cell. At this time stain may also be added by the pipetter station 3. The cells are transported by a settling cell transporter which accepts new settling cells from the settling cell storage area 2 and transports them to the pipetting area 3, to the settling area 4, to the data acquisition area 5, and finally disposes of them in the disposal area 11. The cell transport assembly is used to position the cell during the data acquisition process. This assembly also contains a calibration plate which is used to calibrate the video and image capture apparatus.

Figure 4A:
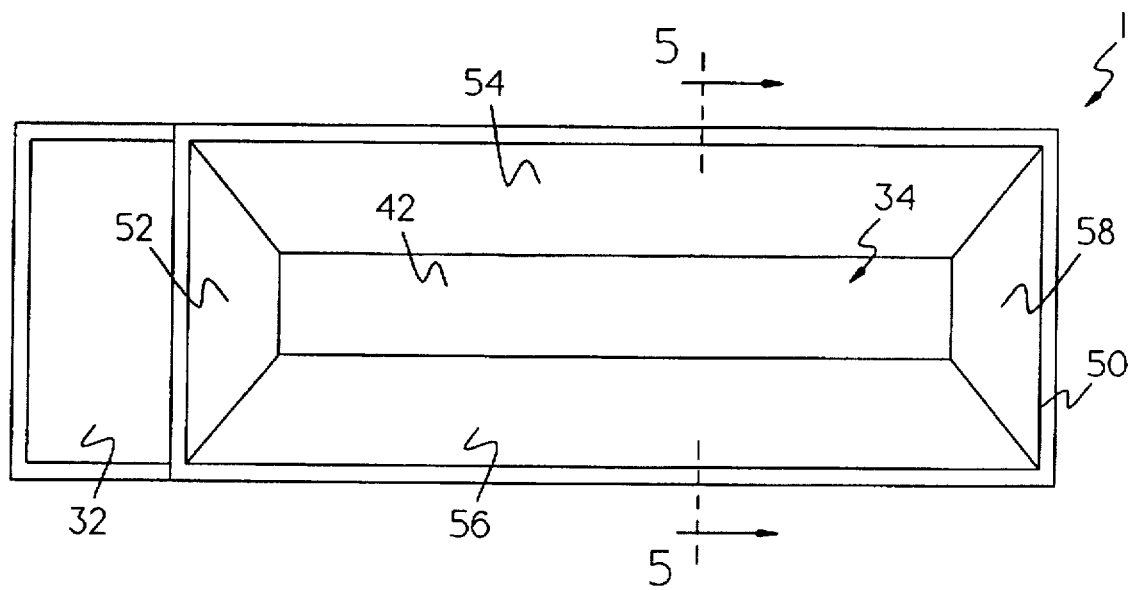
FIGS. 4A and 4B show a top view and a side view of the settling cell of the invention.
Figure 4B:
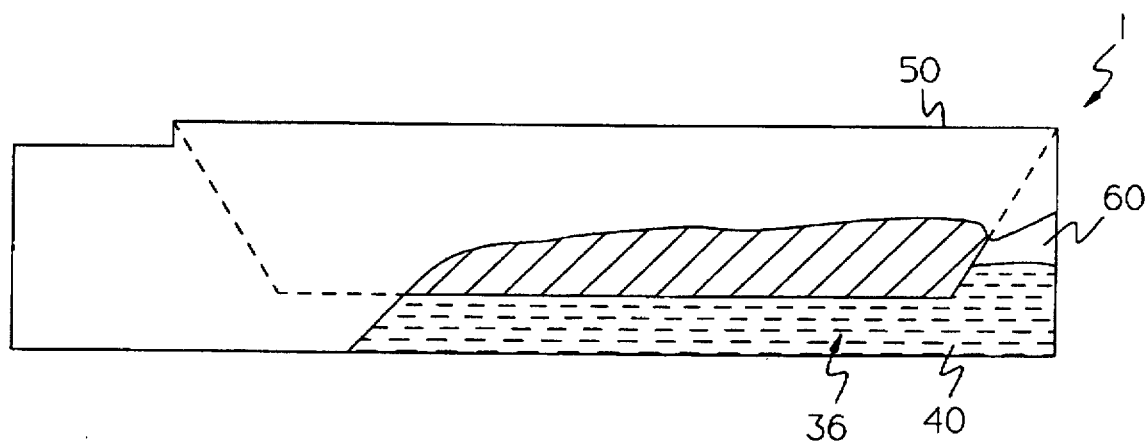

Now referring to FIGS. 4A and 4B, FIG. 4A shows a top view and FIG. 4B shows a partially cut away side view of one of the settling cells 1 of the invention. The settling cell 1 may be comprised substantially of a clear material such as acrylic, plastic, glass or any other equivalent clear material which is suitable for holding a urine sample.

The settling cell 1 is advantageously constructed to comprise a trough shaped region 34, a filling hole 32 and an examination region 36 for holding fluid 40. The filling hole 32 may advantageously be large enough to allow the automatic pipette 17 to deposit a sample into the settling cell. The settling cell 1 may advantageously be designed to hold a sample to be examined, allow for the sediment to settle out, and provide a uniform viewing area. The sample is introduced into the settling cell 1 through the fill hole 32. The examination region 36 is in communication with the filling hole 32 which allows fluid to flow into the examination region 36 where the sediment settles out due to gravity.

Figure 5:
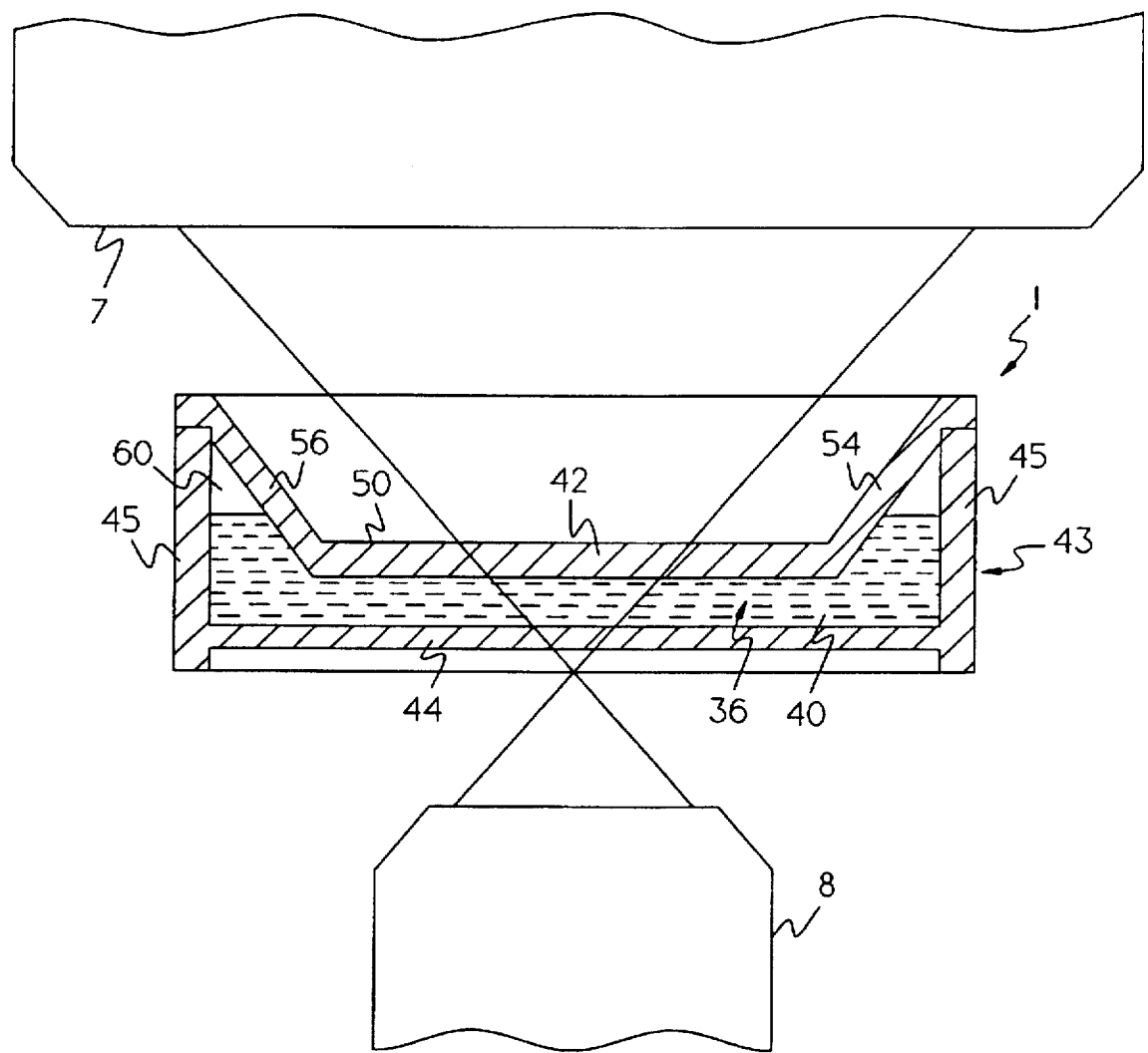
FIG. 5 shows a cross section view of the settling cell of the invention.

Now refer jointly to FIGS. 4A, 4B and 5, where FIG. 5 shows a cross section view of the settling cell of the invention. The trough shaped region 34 comprises a flat surface 42 which is bounded by angled walls 52, 54, 56, and 58 forming top cover 50. Top cover 50 is attached to bottom 43. Bottom 43 comprises bottom wall 44 and bottom sides 45. Examination region 36 comprises a uniform viewing area juxtaposed between the flat surface 42 and a bottom wall 44 in the settling cell 1. Examination region 36 has an area bounded by the perimeter of flat surface 42. In a preferred embodiment of the invention, data is acquired only from fields of view within the examination region 36. The trough-like construction of the settling cell creates a reservoir 60 which surrounds the examination region 36. The reservoir 60 also holds excess fluid. The sample amount pipetted into the filling hole 32 must be enough to fill the examination region 36. Since the reservoir 60 will accept a large amount of excess fluid in relation to the sample size, as long as there is enough fluid to occupy at least a part of the reservoir 60, the amount of fluid in the examination region 36 is uniform. Therefore, a high degree of precision is not needed when metering the fluid into or out of the automatic pipette 17.

In operation, the concentration of the sediment may be calculated by counting the number of objects in each field and using the following equation:

$$C = O/(F*A*H) \tag{1}$$

WHERE:
C=The Concentration in units of Objects Per Volume of Fluid
O=Number of Objects Counted
F=Number of Fields Examined
A=Area of Each Field of View
H=Fluid Height
The amount of fluid that is introduced into the cell is not critical as long as the sample fluid level is higher than the controlled height within examination region 36.

Figure 6:
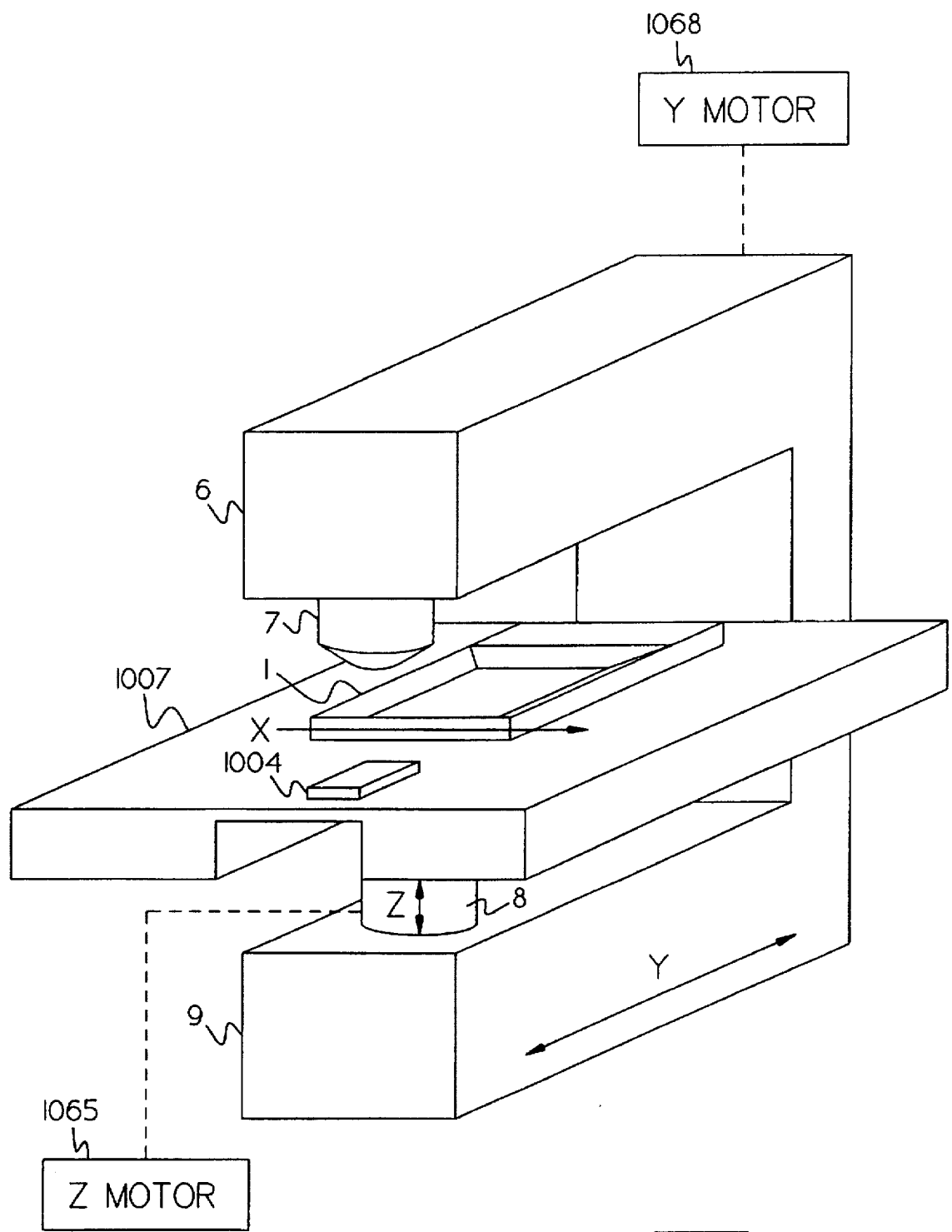
FIG. 6 is a schematic diagram of one embodiment of the inventive apparatus for automated urine sediment sample handling of the invention.

Referring now to FIG. 6, a schematic diagram of one embodiment of the inventive apparatus for automated urine sediment sample handling of the invention is shown. The system there shown includes the illumination assembly 6 having condenser lens 7 mounted thereto. The camera assembly 9 may be rigidly attached to the illumination assembly 6 to form an illumination and camera assembly. A settling cell 1 is shown in position to be scanned by the camera 9. The objective lens 8 is adjustably coupled to camera 9. Also shown is a calibration plate 1004 on a stage 1007. The calibration plate 1004 includes image primitives suitable for characterizing the imaging system. See, for example, U.S. Pat. No. 5,361,140 issued Nov. 1, 1994 to Hayenga et al., entitled "METHOD AND APPARATUS FOR DYNAMIC CORRECTION OF MICROSCOPIC IMAGE SIGNALS".

Motion is indicated along X, Y and Z axes. The motion in each axis may be implemented by a different system. Motion along the Y axis is done by moving the illumination and camera assembly using the Y motor 1068. Motion along the Z axis is done by using Z motor 1065 to move the objective lens 8. In operation, a settling cell 1 rests on a stage 1007 and is moved in a direction along the X axis by the transport system 15 shown in FIG. 1, for example. The illumination assembly 6, the camera assembly 9, the condenser lens 7 and the objective lens 8 are moved together along the Y axis. The calibration plate 1004 may also be imaged using a Y direction motion. The objective lens 8 is moved in a direction along the Z axis to keep the sample in focus.

In operation, the stored image from the camera 9 is converted into digital information. Corrections are applied to the information in order to correct for spatial and temporal inconsistencies in the illumination, objective lens 8, and camera 9. These corrections are determined during a periodic calibration process by using the calibration plate 1004 as a reference and making appropriate adjustments in accordance with known practice or as disclosed in patent application Ser. No. 08/309,249, filed Sep. 20, 1994 and now abandoned, to Ortyn et al., entitled "BIOLOGICAL SPECIMEN ANALYSIS SYSTEM PROCESSING INTEGRITY CHECKING APPARATUS" and in U.S. Pat. No. 5,361,140 issued Nov. 1, 1994 to Hayenga et al., entitled "METHOD AND APPARATUS FOR DYNAMIC CORRECTION OF MICROSCOPIC IMAGE SIGNALS".

Figure 7:
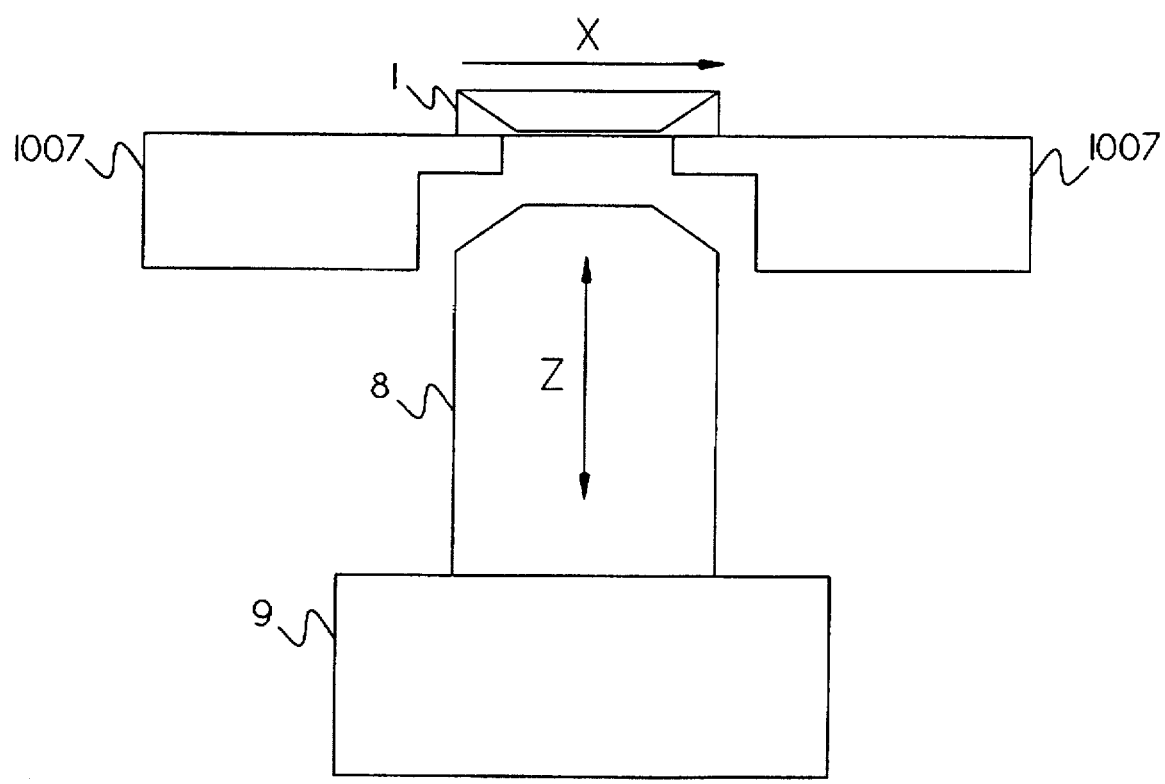
FIG. 7 shows schematically a section view of the embodiment of the inventive apparatus of FIG. 6.

Now referring to FIG. 7, a sectioned view through the stage 1007, the settling cell 1 and the objective lens 8 of one embodiment of the inventive apparatus for automated urine sediment sample handling of FIG. 6 is shown.

Figure 8B:
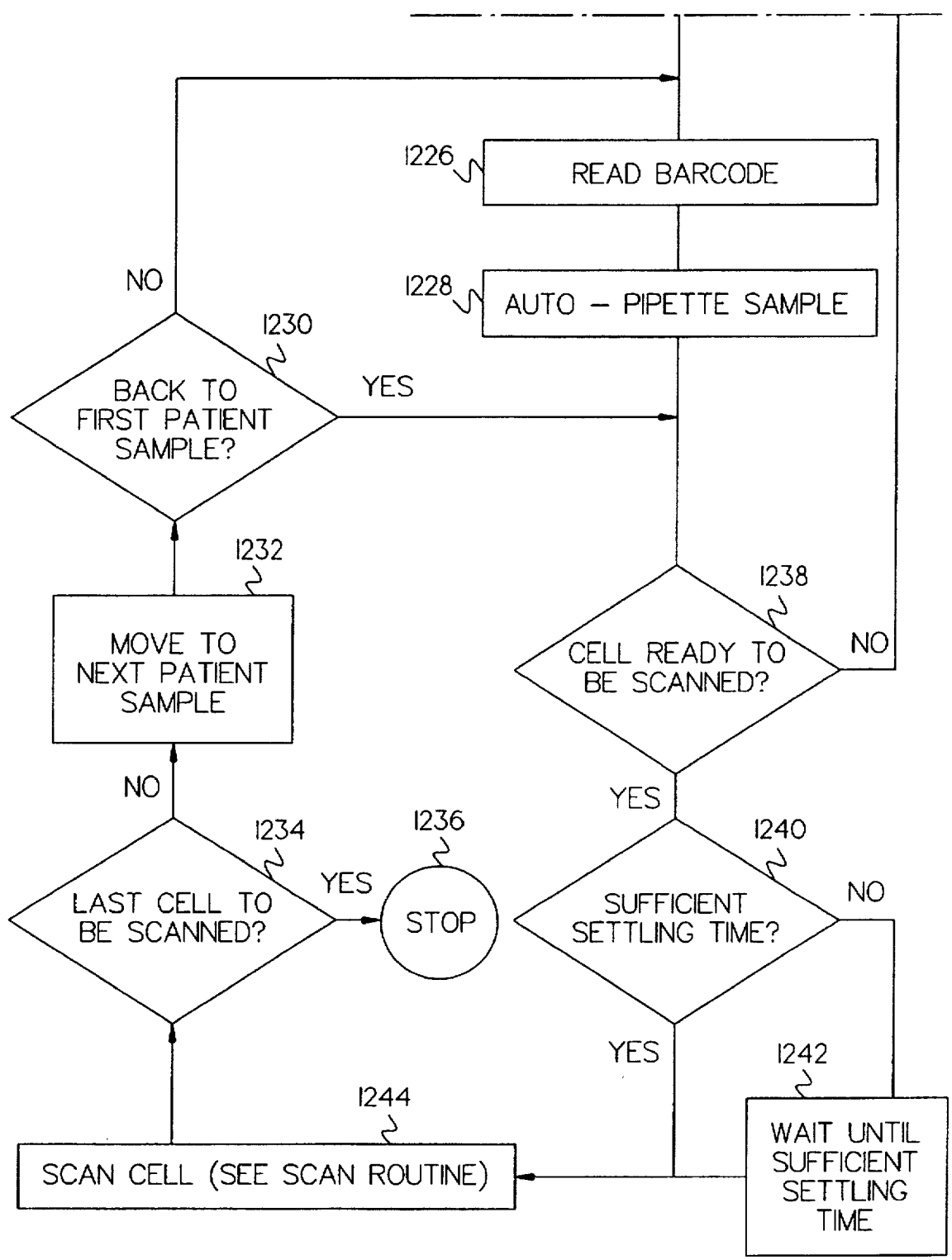
FIG. 8 shows the alignment of FIGS. 8A and 8B which in turn show a method flow diagram illustrating steps for operating an automated urine sediment sample handling system in accordance with the subject invention.

Now referring to FIG. 8 and more specifically in FIGS. 8A and 8B, a method flow diagram illustrating steps for operating an automated urine sediment sample handling system in accordance with the subject invention is shown. At step 1210 the user or operator turns the system on. A self test may then be executed by the main processor 1020 at step 1212 to verify that the system is operational. Such a self test may consist of polling the various components to ascertain a GO/NOGO signal, for example. Calibration may be implemented automatically at step 1214. At step 1216 sample containers of patient samples are manually loaded into the sample carrier 12. Several samples may be added to the sample carrier at one time. At step 1218 the user loads the settling cell storage area 2 with unused cells.

At step 1220, the system is activated by the user by pushing a start button, for example. At step 1222 an empty settling cell is moved into pipetting position. At step 1224 the patient sample carrier 12 is moved to the next patient sample. At step 1226 the next sample in line is moved to the barcode reader 14 where the barcode is read. Then at step 1228, an automatic pipette 17 extracts a portion of the sample and transfers it to the settling cell 1 which has been moved from the settling cell storage area 2 to a position across from the sample.

At step 1238 the data acquisition area 5 is checked for the presence of a settling cell to be scanned. If no settling cell is ready to be scanned the process returns to step 1222. If a settling cell is in position to be scanned, a decision is made at step 1240 determining whether a sufficient amount of settling time has elapsed. The appropriate settling time may be a predetermined time period which provides enough time for the sample in the settling cell to settle. If more settling time is needed, the process will wait at step 1242 for the amount of time required. The sample is moved to a storage area where the sediment is allowed to settle under the effects of gravity. During this time the next patient sample may be moved into position and a portion of the next patient sample may be transferred to the next settling cell. After the settling time has elapsed, the settling cell is scanned at step 1244. The scanning routine is described in more detail with respect to FIG. 9 and more specifically in FIGS. 9A and 9B. When being scanned, the settling cell is positioned between the condenser lens 7 and the objective lens 8. The illumination assembly 6 illuminates the cell through the condenser lens 7. The image of the sediment within the cell is captured through the objective lens 8 by the CCD video camera 9. The video information is transformed into digital information by the image processor 10.

If the last cell scanned exhausts the number of settling cells to be scanned, a decision is made at step 1234 to end the process at step 1236 or proceed to the next patient sample at step 1232. At step 1230 a decision is made as to whether all patient samples the patient samples have been pipeted. If all patient samples have been pipeted, the process returns to step 1238. If more patient samples are to be pipeted, the process returns to step 1226. In one embodiment of the invention, the cells are optionally dropped into the disposal area 11 after they have been examined.

Figure 9B:
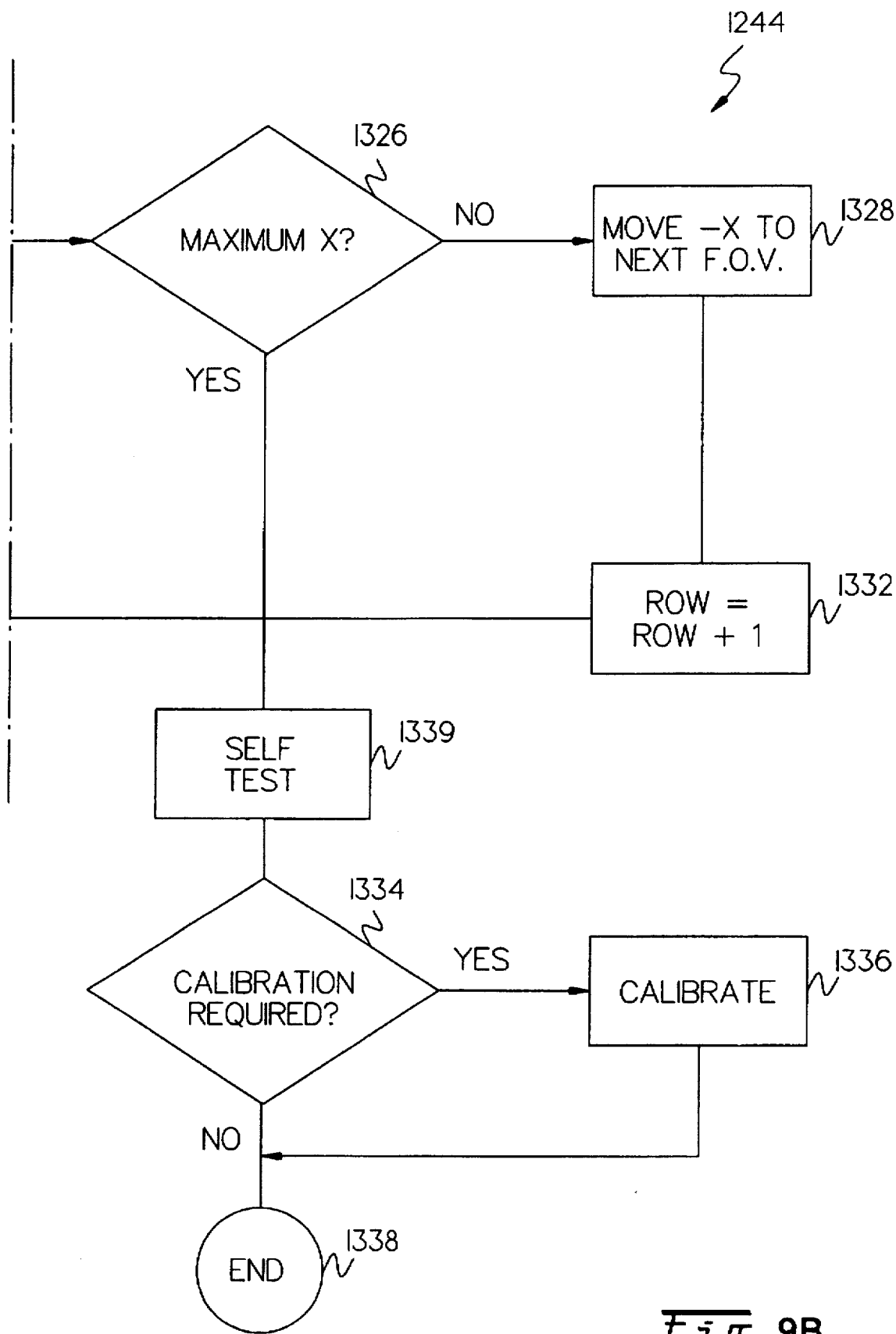
FIG. 9 shows the alignment of FIGS. 9A and 9B which in turn show a method flow diagram illustrating steps for scanning as employed in one embodiment of an automated urine sediment sample handling system in accordance with the subject invention.

Refer now to FIG. 9 and more specifically in FIGS. 9A and 9B where a process flow diagram for scanning as employed in one embodiment of an automated urine sediment sample handling system is shown. Also refer to FIG. 10 which schematically illustrates a method for scanning as employed in one embodiment of an automated urine sediment sample handling system in accordance with the subject invention. The scanning process begins at step 1310. At step 1312 the scanning process is initialized by setting a row value equal to 1.

Figure 10:
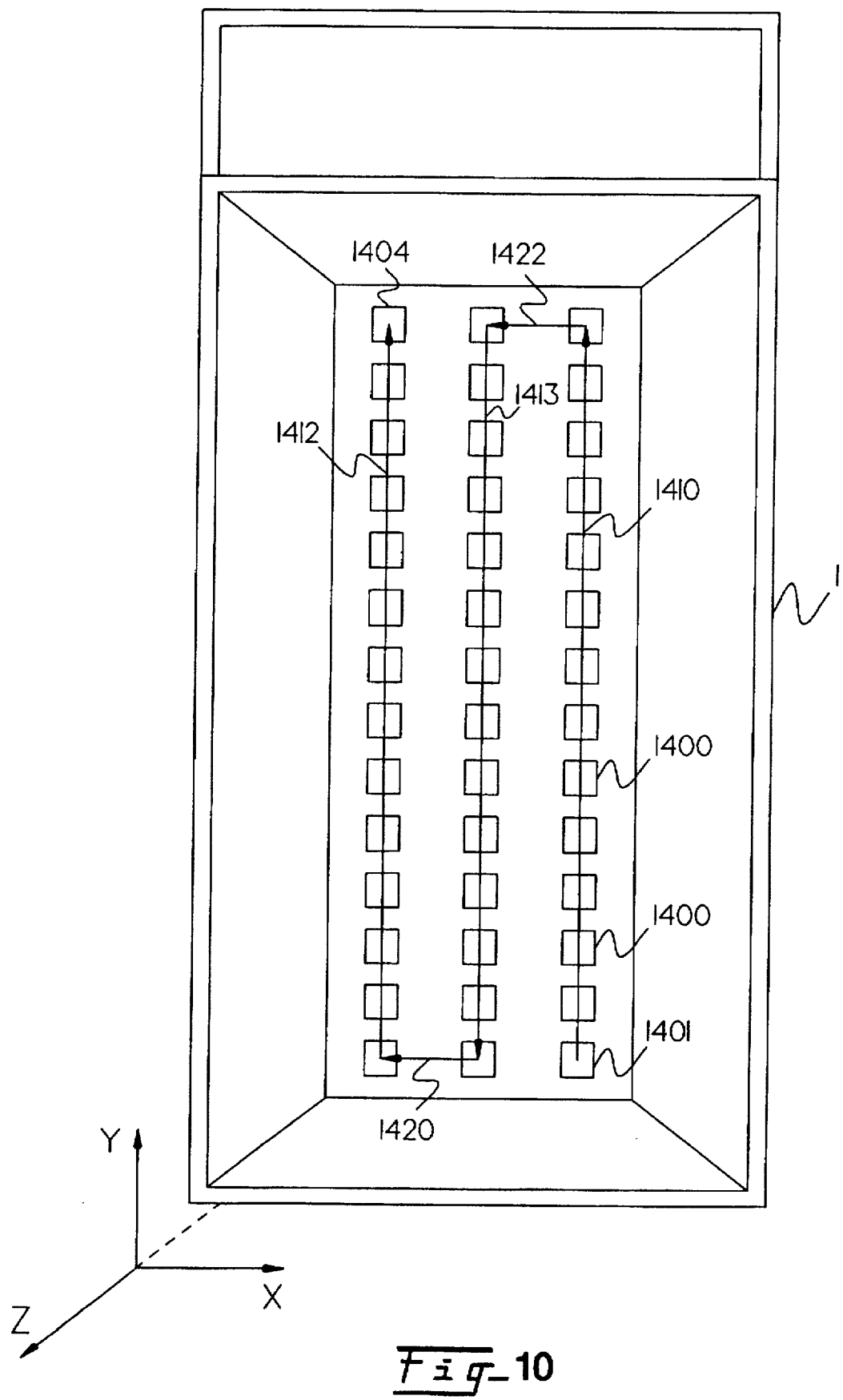
FIG. 10 schematically illustrates a method for scanning as employed in one embodiment of an automated urine sediment sample handling system in accordance with the subject invention.

See FIG. 10 which schematically shows a settling cell 1 having a number of fields of view 1400 which are arranged in a plurality of rows and columns. In this example a small number of rows and columns have been shown to facilitate an understanding of the invention with an uncluttered drawing. Those skilled in the art will recognize that this example is by way of illustration and in no way so limits the invention. In an operating system thousands of fields of view may be used if desired. Moves in the X and Y directions are in reference to a Cartesian coordinate system as indicated by the XYZ coordinates shown adjacent the settling cell 1. Moves in a positive Y direction are indicated by directional arrows 1410 and 1412. Moves in the negative Y direction are indicated by directional arrow 1413. Moves in the X direction are indicated by directional arrows 1420 and 1422. Movement of the settling cell is preferably done one field of view (F.O.V.) 1400 at a time starting with a first field of view 1401 and ending with a last field of view 1404. At step 1314 the objective lens 8 is focussed on a preselected first field of view 1401. Step 1316 checks whether the current row is even. If the current row is odd, as in the case of row 1, the process proceeds to step 1318 where a move is made in the positive Y direction. The process then proceeds to step 1322 which checks for the maximum Y position. If the subject field of view is at the maximum Y position the process is routed to step 1326. If the subject field of view is not at the maximum Y position, the process flows to step 1330 for further processing. The digital information which represents the image of sediment is now ready for evaluation. The process then returns to step 1316 to obtain the next target field of view.

If at step 1316 the current row number is even, the process goes to step 1320 and a move in the minus Y direction is made at step 1320. At step 1324 the process verifies whether the current Y position is the minimum Y position. If it is not the minimum Y position, the process goes to step 1330 and continues as described above. If it is the minimum Y position, the process goes to step 1326 and the process verifies whether the current X position is the maximum X position. If it is not the maximum X position, the process goes to step 1328 where a move is made in the X direction to the next field of view. The row is incremented at step 1332 and the process continues through step 1330 as before.

If it is the maximum X position and the maximum Y position, the last field of view 1404 has been scanned and the process may optionally move to a self test at step 1339 followed by a check for required calibration at step 1334. If calibration is indicated the process goes to step 1336. The process ends at step 1338 and returns to the main system process at step 1234.

Refer now to FIGS. 11 and 12 which show a schematic diagram of one embodiment of a transport mechanism employing a tape 1118 and reel 1123. The transport system 1115 comprises a tape 1118 and feed reel 1123 to move settling cells 1. The settling cell 1 may be attached to two strips of plastic tape 1116A and 1116B which have perforations 1117 similar to those used in photographic film. These strips are attached in areas that do not interfere with the examination area of the settling cell 1. The tape 1118 and settling cells 1 are wound around a feed reel 1123. The tape 1118 is threaded through a series of sprockets 1112 and 1114. The sprockets 1112 and 1114 serve to position the settling cells 1. The cells may pass through the sample pipetting area, the settling area 4 and the examination area as shown in FIG. 2. At the examination area, the transport system 1115 provides motion along the X axis for the examination. After the settling cell leaves the examination area, the sprockets 1114 guide them onto a take-up reel 1122. When the settling cells 1 have all been transported to the take-up reel, the reel is removed and discarded.

Figure 13:
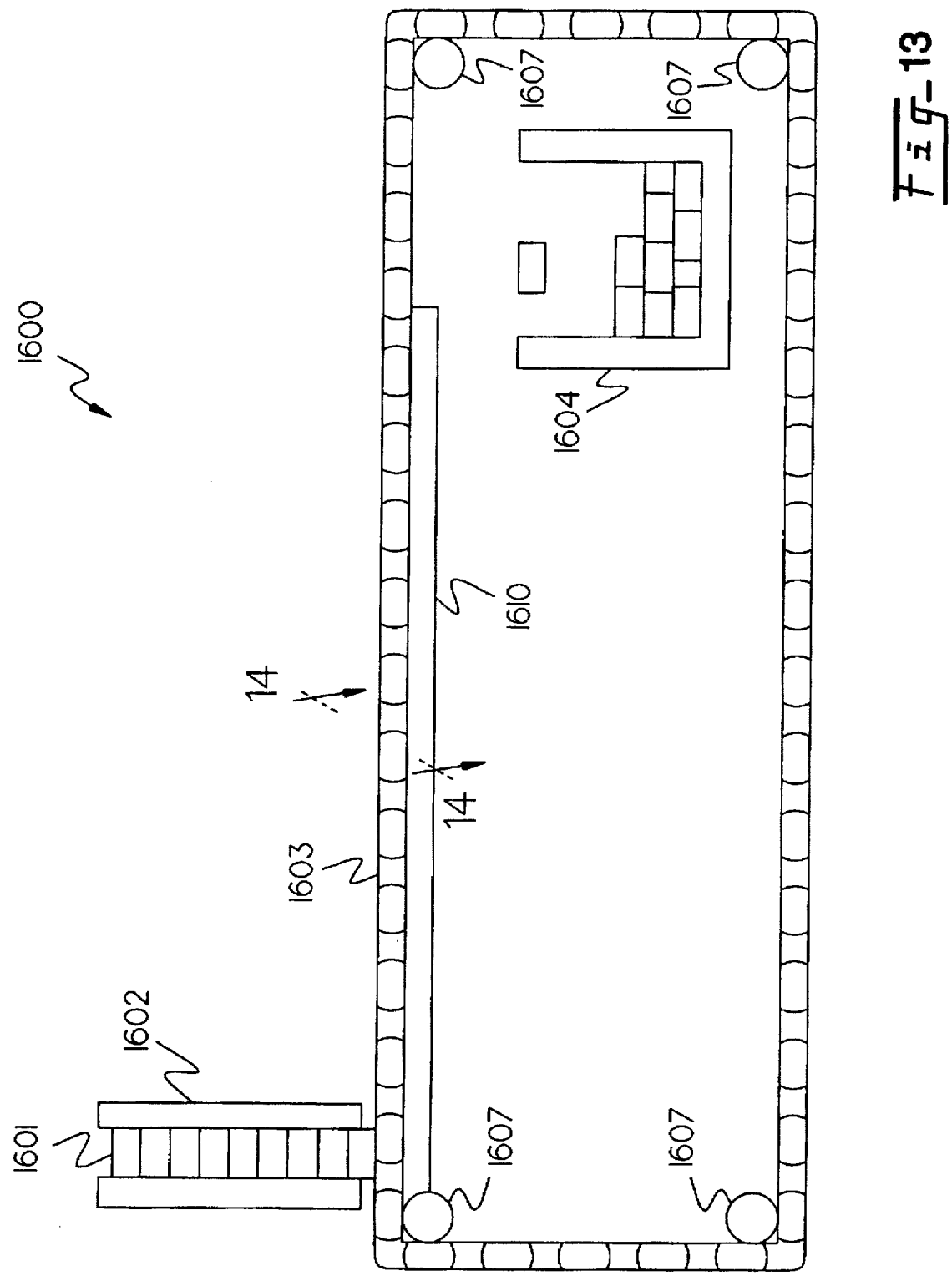
FIGS. 13 and 14 show a schematic diagram with an enlarged view of one embodiment of a transport mechanism employing a chain drive as may be employed in an alternate embodiment of the inventive apparatus for automated urine sediment sample handling of the invention.
Figure 14:
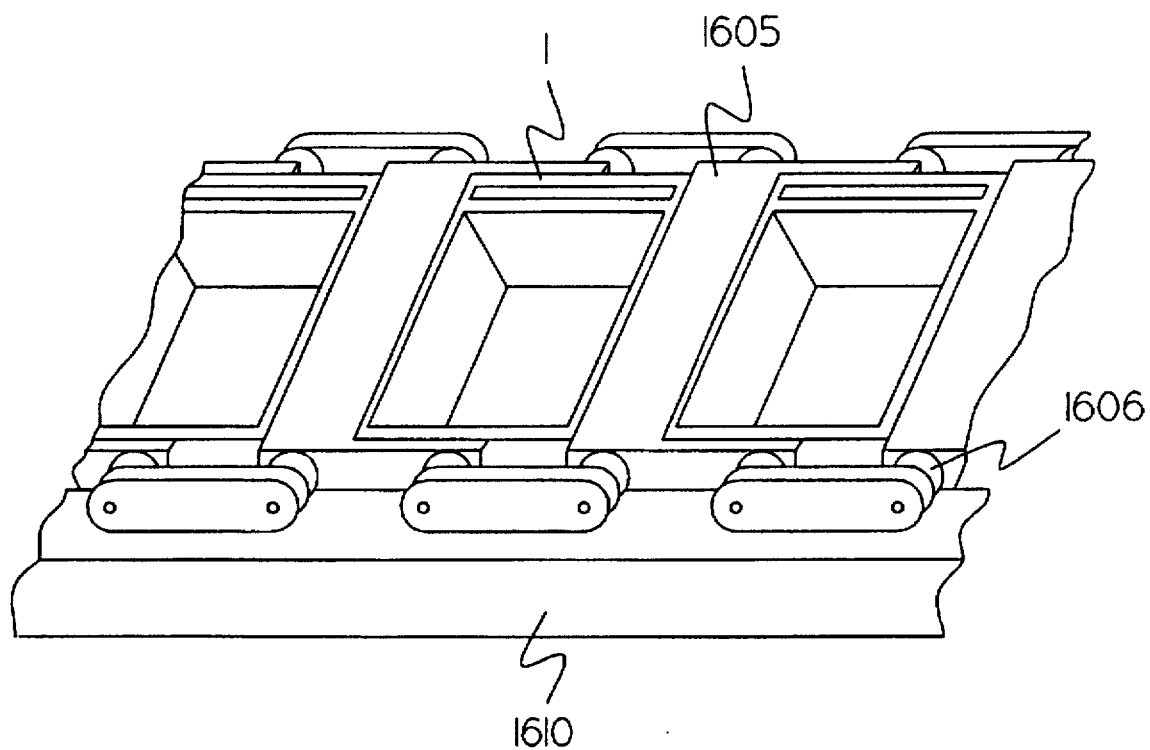

FIGS. 13 and 14 show a schematic diagram of an alternate embodiment of a transport mechanism employing a chain drive. The chain drive mechanism 1600 comprises a chain drive 1603 including parallel chain rollers 1606 and cradles 1605 for carrying settling cells 1. Parallel rails 1610 may be used in cooperation with the cradle 1605 to hold the settling cells 1 in position while allowing movement along one direction. The settling cells 1 are stored in an input bin 1601 with a feeding mechanism 1602. The bottom settling cell in the bin 1601 is dropped by the feeding mechanism 1602 on the chain drive 1603 as an empty position passes under the bin 1601. The cell cradle 1605 moves the settling cell along to the sample pipetting area, the settling area 4, and the examination area. At the examination area, the transport system 1115 provides motion along the X axis for the examination. The chain may be moved by sprockets 1607, for example, which engage the parallel chain rollers 1606. As the settling cell passes over a disposal bin 1604, the settling cell 1 drops in.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An automated apparatus for urine sediment sample handling comprising:
   (a) a plurality of settling cells for carrying patient samples;
   (b) a sample and cell transport assembly for transporting the plurality of settling cells in one direction through an examination area;
   (c) an illumination and camera assembly positioned in the examination area to view one of the plurality of settling cells when one of the plurality of settling cell moves to the examination area, said illumination and camera assembly having a first data output;
   (d) an image processing assembly coupled to receive data from said first data output, the image processing assembly having a second data output for carrying processed digital data; and
   (e) a processor having a plurality of control lines coupled to said sample and cell transport assembly, illumination and camera assembly, and image processing assembly, wherein said sample and cell transport assembly, illumination and camera assembly, and image processing assembly operate responsively to commands from said processor to handle urine sediment samples.

2. The automated apparatus for urine sediment sample handling of claim 1 further comprising a disposal bin positioned to receive the plurality of settling cells from the sample and cell transport assembly.

3. The automated apparatus for urine sediment sample handling of claim 1 further comprising:
   (a) a storage bin located at a forward end of said examination area where empty sample cells are stored in said storage bin;
   (b) means for automatically loading the empty sample cells from said storage bin onto said sample and cell transport assembly;
   (c) an automatic pipette located in a pipetting area which is located between said examination area and said storage bin; and
   (d) a sample carrier located adjacent said automatic pipette, wherein said processor further has a second plurality of control lines coupled to said storage bin, automatic pipette and sample carrier, wherein said storage bin, automatic pipette and sample carrier are responsive to control signals from said processor such that, under control of said processor, a sample may be removed by said automatic pipette from a patient sample in the sample carrier and placed into an empty settling cell in said pipetting area.

4. The automated apparatus for urine sediment sample handling of claim 1 wherein the sample and cell transport assembly further comprises:
   (a) at least one drive tape to hold the plurality of settling cells, wherein the at least one drive tape has sprocket holes; and
   (b) a sprocket drive for driving the at least one drive tape.

5. The automated apparatus for urine sediment sample handling of claim 1 wherein the sample and cell transport assembly further comprises:
   (a) a transport chain;

(b) a chain drive connected to drive the transport chain; and (c) at least one cradle to hold the plurality of settling cells, wherein the at least one cradle is connected to the transport chain.

6. An automated method for operating an automated urine sediment sample handling system under control of a computer processor, the automated method comprising the steps of:

(a) moving a settling cell into a pipetting position, wherein the settling cell has a viewing area, wherein the viewing area is divided into a plurality of fields of view;

(b) moving a patient sample carrier to present a next patient sample;

(c) extracting a predetermined portion of the next patient sample by operating an automatic pipette;

(d) transferring the predetermined portion to the settling cell;

(e) checking a data acquisition area for the settling cell containing a sample to be scanned;

(f) if no settling cell is ready to be scanned returning to step e;

(g) waiting until a predetermined settling time period has elapsed;

(h) scanning the settling cell; and (i) analyzing the plurality of fields of view within the viewing area of said settling cell.

7. The automated method of claim 6 further comprising the steps of:

(a) verifying that the automated urine sediment sample handling system is operational; and (b) executing a calibration routine.

8. An automated method for urine sediment sample handling under computer control to position a settling cell between a condenser lens and an objective lens, the automated method comprising the steps of:

(a) placing a sample container having a barcode onto a sample carrier, wherein the sample container contains a patient sample;

(b) reading the barcode by operation of a barcode reader under computer control;

(c) automatically extracting a sample portion of the patient sample using an automatic pipette under computer control;

(d) transferring the sample portion to a first settling cell;

(e) performing steps (a)–(d) for a next sample while the first sample is settling; and (f) positioning the first settling cell between the condenser lens and the objective lens.

9. The automated method for urine sediment sample handling of claim 8 further comprising the steps of automatically dropping the first settling cell into a disposal area after the step of positioning the first settling cell between a condenser lens and an objective lens.

* * * * *

UNITED STATES PATENT AND TRADEMARK OFFICE
CERTIFICATE OF CORRECTION

PATENT NO. : 5,699,794
DATED : December 23, 1997
INVENTOR(S) : Fleck

It is certified that error appears in the above-indentified patent and that said Letters Patent is hereby corrected as shown below:

Column 3, line 23, after the word "about" insert -- 14%, --.

Column 3, line 26, delete the first occurrence of the word "method".

Column 10, line 25, delete the first occurrence of the phrase "patient samples".

Column 10, line 26, delete both occurrences of the word "pipeted" and replace it with -- pipetted --.

Column 10, line 28, delete the word "pipeted" and replace it with -- pipetted --.

Column 10, line 59, delete the word "focussed" and replace it with -- focused --.

Signed and Sealed this

Twenty-ninth Day of September, 1998

Attest:

BRUCE LEHMAN

*Attesting Officer*  *Commissioner of Patents and Trademarks*